United States Patent [19]

Kipnis et al.

[11] Patent Number: 5,097,997
[45] Date of Patent: Mar. 24, 1992

[54] BI-DIRECTIONAL BELT CLIP FOR PORTABLE WEARABLE DEVICES

[75] Inventors: Alexander Kipnis, Minneapolis; Zosim Ioffe, St. Paul, both of Minn.

[73] Assignee: Empi, Inc., St. Paul, Minn.

[21] Appl. No.: 366,127

[22] Filed: Jun. 12, 1989

[51] Int. Cl.⁵ .................... A45F 5/00; A44B 21/00
[52] U.S. Cl. .................... 224/269; 224/195; 224/252; 224/253; 24/3 J; 24/163 K; 248/229; 248/231.8; 248/207
[58] Field of Search ........... 224/269, 195, 224, 225, 224/247, 252, 253, 242, 245, 249, 904, 240, 163; 24/3 R, 3 J, 3 L, 563, 163 K; 248/229, 231.8, 207; 2/94, 304, 305, 319

[56] References Cited

U.S. PATENT DOCUMENTS

| | | | |
|---|---|---|---|
| 822,076 | 5/1906 | Rhodes | 2/319 |
| 1,342,666 | 6/1920 | Crouch | 2/305 |
| 2,387,900 | 10/1945 | Hartwell | |
| 2,970,448 | 2/1961 | Di Julio | 224/269 |
| 3,631,994 | 1/1972 | Mackzum, Jr. | 224/26 R |
| 3,642,184 | 2/1972 | Hendricks | 224/2 C |
| 3,878,589 | 4/1975 | Schaefer | 224/269 |
| 4,214,688 | 7/1980 | Griffin, Jr. | 224/197 |
| 4,299,344 | 11/1981 | Yamashita et al. | 224/252 |
| 4,403,717 | 9/1983 | Glover | 224/252 |
| 4,485,946 | 12/1984 | Liautaud et al. | 224/242 |
| 4,605,335 | 8/1986 | Otrusina | 403/348 |
| 4,635,836 | 1/1987 | Mooney et al. | 224/247 |
| 4,718,586 | 1/1988 | Hagino | 224/252 |
| 4,770,328 | 9/1988 | Dickhudt et al. | 224/252 |
| 4,828,153 | 5/1989 | Guzik et al. | 224/269 |
| 4,872,600 | 10/1989 | Corbin | 224/245 |

Primary Examiner—Henry J. Recla
Assistant Examiner—Keith Kupferschmid
Attorney, Agent, or Firm—Kinney & Lange

[57] ABSTRACT

A bi-directional clip. The clip includes a generally planar member having an edge and fastener for securing the planar member to a portable wearing device. An elongated slot extends through the planar member from the edge to form a pair of clip members.

12 Claims, 2 Drawing Sheets

BI-DIRECTIONAL BELT CLIP FOR PORTABLE WEARABLE DEVICES

BACKGROUND OF THE INVENTION

1. Field of the Invention

The present invention relates generally to belt clips for securing portable wearable devices to garments of the user.

2. Description of the Prior Art

Belt clips are commonly used to attach small, relatively light weight, and portable devices such as pagers, radios, and transcutaneous electrical nerve stimulators (TENS) to the user's belt or waist band. One known belt clip distributed by EMPI, Inc., the assignee of the present invention, along with its TENS units, is a one-piece plastic clip which includes a generally U-shaped fastener which extends around the unit and includes tabs which resiliently engage recesses on the side of the unit. A clip member extends in a generally perpendicular direction from the U-shaped fastener along the back wall of the unit for engagement with the user's belt. Other belt clips are disclosed in the following United States patents:

| U.S. Pat. No. | Inventor(s) | Issue Date |
|---|---|---|
| 2,387,900 | Hartwell | October 30, 1945 |
| 3,631,994 | Mackzum, Jr. | January 4, 1972 |
| 3,642,184 | Hendricks | February 15, 1972 |
| 4,214,688 | Griffin, Jr. | July 29, 1980 |
| 4,485,946 | Liautaud et al. | December 4, 1984 |
| 4,605,335 | Otrusina | August 12, 1986 |
| 4,635,836 | Mooney et al. | January 13, 1987 |
| 4,718,586 | Hagino | January 12, 1988 |

The manner in which patients wear their TENS units depends upon function, comfort, and aesthetic concerns. Some patients prefer to have their stimulators attached vertically with the control knobs extending upward, while others prefer a horizontal orientation with the control knobs extending forward. Stimulators with belt clips which can accomodate these different preferences are available. However, they generally require some disassembly of the belt clip. Typically, this is done by loosening a screw or even moving the clip altogether before it is reoriented and reattached in a desired manner. Clips of this type are therefore inconvenient to use. The screw assemblies are also sometimes bulky, further detracting from the desirability of these clips.

It is evident that there is a continuing need for improved belt clips. Specifically, there is a need for a belt clip which can be conveniently used to attach a portable wearable device at a desirable orientation to a garment of the user. A belt clip of this type must be capable of securely attaching the portable device to the garment, but should be relatively inexpensive to manufacture.

SUMMARY OF THE INVENTION

The present invention is a bi-directional belt clip for securing a portable wearable device to garments of a user. The clip includes a generally planar member having an edge, a fastener for securing the planar member to the portable wearable device, and an elongated slot extending through the planar member from the edge to form a pair of clip members.

In one embodiment, the planar member is spaced from and generally parallel to the portable wearable device. The fastener is a resilient and a generally U-shaped member having inwardly facing lugs for engaging opposite sides of the portable wearable device. The planar member is generally rectangular and the slot extends diagonally across the planar member. In another embodiment, the clip includes an enlarged aperture extending through the planar member and communicating with an end of the slot opposite the edge of the planar member.

BRIEF DESCRIPTION OF THE DRAWINGS

FIG. 3b is an illustration of the belt clip shown in FIG. 1 attached to the belt in a horizontal orientation.

DETAILED DESCRIPTION OF THE PREFERRED EMBODIMENTS

Figure 1:
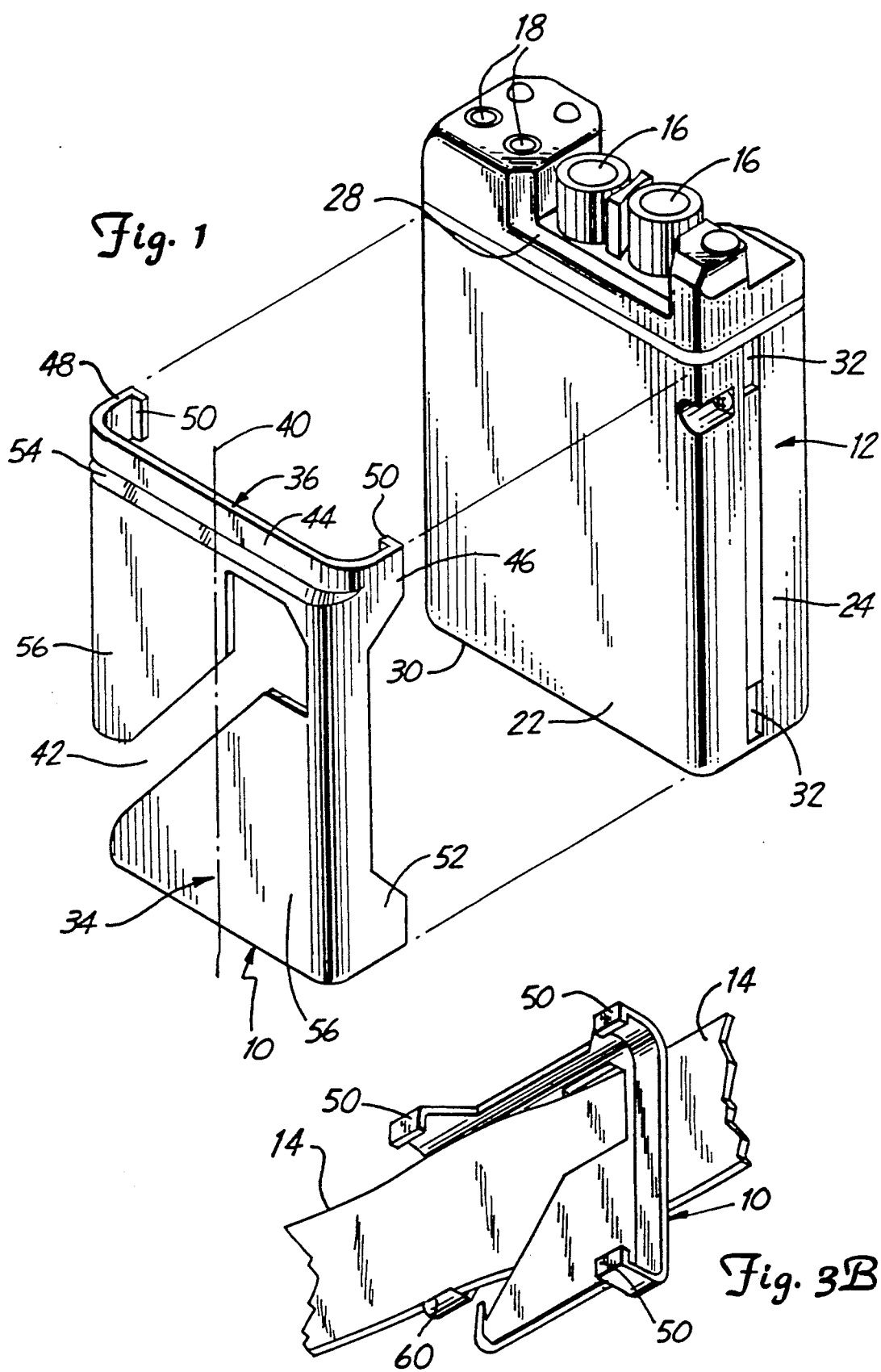
FIG. 1 is an exploded perspective view of a belt clip in accordance with the present invention shown in conjunction with a stimulator to which it can be attached.
Figure 2:
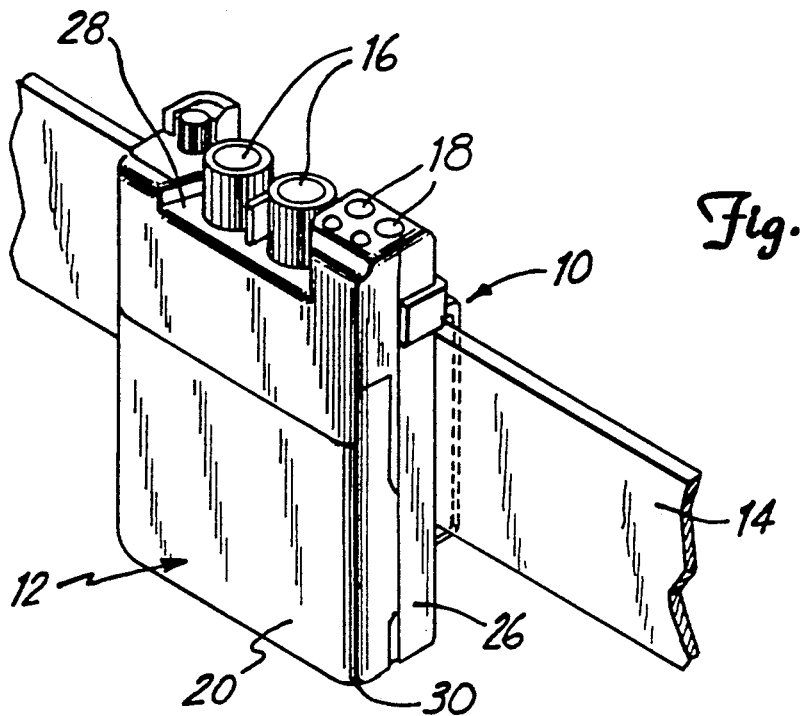
FIG. 2 is a perspective view of a stimulator and belt clip in accordance with the present invention attached to a belt.

A bi-directional belt clip 10 in accordance with the present invention is illustrated generally in FIGS. 1-4. Belt clip 10 is used to secure a portable wearable device such as a transcutaneous electrical nerve stimulator or TENS unit 12 to the edge of a garment such as belt 14 worn by a user (not shown). TENS unit 12, like most of the portable wearable devices, is asymmetric and includes members such as control knobs 16 and terminals 18 on one side thereof. These members must be accessible to the user. For reasons which can be influenced by comfort, function, or aesthetic considerations, some patients prefer to wear their stimulator 12 in a vertically oriented position, such as that shown in FIGS. 2, 3a and 4 while others prefer to wear their stimulator in a horizontal position such as that shown in FIG. 3b. Using belt clip 10, a patient can conveniently attach stimulator 12 to belt 14 in either a horizontal or a vertical orientation.

Stimulator 12 has a generally rectangular shape and includes front wall 20, back wall 22, left side wall 24, right side wall 26, top wall 28, and bottom wall 30. Control knob 16 and terminals 18 extend from top wall 28. Side wall 24 has recesses 32 formed therein, one near top wall 28 and another near bottom wall 30. A recess 32 is similarly formed in side wall 26 near top wall 28.

Belt clip 10 includes a generally planar belt-receiving member 34 and a fastener 36 for securing a belt clip to stimulator 12. Belt clip 10 is configured about an imaginary clip axis 40. In the embodiment shown, the belt clip 10 is configured in such a manner that axis 40 will extend in a perpendicular direction from top wall 28 and bottom wall 30 when belt clip 10 is secured to stimulator 12.

Figure 3A:
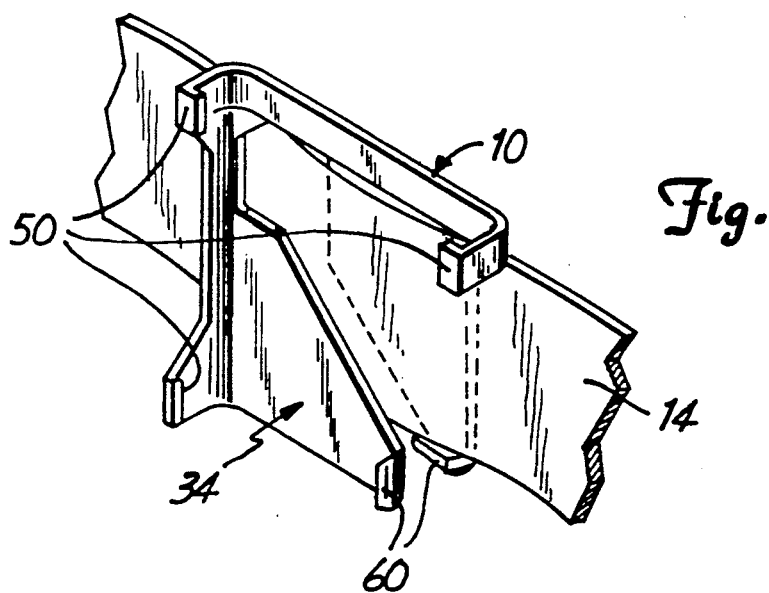
FIG. 3a is an illustration of the belt clip shown in FIG. 1 attached to the belt in a vertical orientation.
Figure 4:
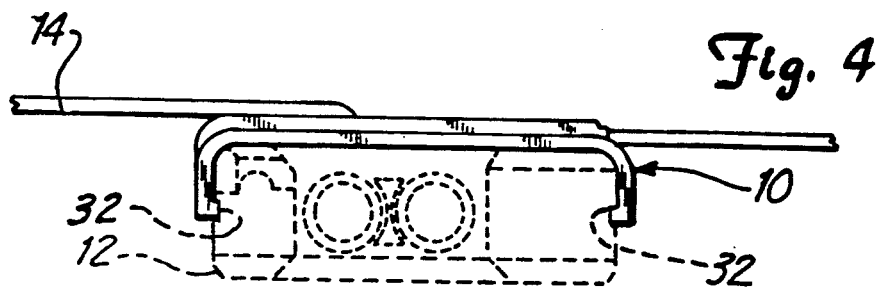
FIG. 4 is a top plan view of the belt clip shown in FIG. 1 attached to the belt with the stimulator shown in phantom.

In the embodiment shown, fastener 36 includes a U-shaped member formed by wall portions 44, 46, 48 and 52. Wall portion 44 fits against back wall 22 of stimulator 12, while wall portions 46 and 48 extend around side walls 24 and 26, respectively. Wall portions 46 and 48 terminate with inwardly extending tabs 50. Wall portion 52 extends from planar member 34 at a location displaced from wall portion 46 along axis 40. As shown in FIGS. 3a and 3b wall portion 52 also terminates with a tab 50. Stimulator 12 is secured to belt clip 10 when tabs 50 of fastener 36 are resiliently engaged with the corresponding recesses 32 in the stimulator.

Section 54 extends from planar member 34 to wall portion 44 of fastener 36. Planar member 34 is thereby positioned in a spaced-parallel relationship to back wall 22 when clip 10 is attached to stimulator 12. In one embodiment, planar member 34 is spaced from back wall 22 by approximately one-eight inch.

As shown in FIG. 1, a slot 42 in planar member 34 extends into the planar member from one of its corners or edges. In the embodiment shown in FIG. 1, slot 42 extends into planar member 34 at approximately a 45° angle from the corner and is approximately three-eighths of an inch wide. A pair of clip sections 56 are formed from planar member 34 by slot 42. Slot 42 ends in an enlarged opening 58 through planar member 34. Opening 58 is situated in a corner of planar member 34. As perhaps best shown in FIG. 3a, a tab 60 also extends from the back of each clip section 56 at a location near the intersection of slot 42 and the edge of planar member 34. Tabs 60 are sized so as to rest on back wall 22 of stimulator 12 after the clip has been attached to the stimulator.

In preferred embodiments, belt clip 10 is molded from plastic material as a one-piece unit. Tabs 50 of fastener 36 are snapped into recesses 32 to resiliently secure belt clip 10 to stimulator 12. Using belt clip 10 a patient can conveniently mount stimulator 10 to belt 14 in either the vertically or horizontally oriented position.

Although the present invention has been described with reference to preferred embodiments, workers skilled in the art will recognize that changes may be made in form and detail without departing from the spirit and scope of the invention.

What is claimed is:

1. A bi-directional clip configured to engage an edge of a user's garment including:
   a generally planar member having peripheral edges;
   fastener means connected to the planar member for securing the planar member to a portable wearable device; and
   an elongated slot extending diagonally through a substantial portion of the planar member relative to the peripheral edges of the planar member; said slot extends through one peripheral edge of the planar member to form a pair of clip members that accept the edge of the user's garment, through the slot.

2. The clip of claim 1 wherein the fastener means includes means for securing the planar member to the portable device with the planar member spaced from the portable device.

3. The clip of claim 2 wherein the planar member further includes at least one tab extending from each clip member for engaging the portable device.

4. The clip of claim 1 wherein the fastener means includes means for securing the planar member to the portable device with the planar member spaced from and generally parallel to the portable device.

5. The clip of claim 1 and further including an enlarged aperture extending-through the planar member and communicating with an end of the slot opposite the peripheral edge of the planar member.

6. The clip of claim 5 wherein the fastener means includes a resilient generally U-shaped member having inwardly facing lugs for engaging opposite sides of the portable device.

7. The clip of claim 1 wherein the clip is a one-piece unit fabricated of plastic.

8. A one-piece bi-direction clip for securing a portable wearable device to an edge of a user's garment in either vertical or horizontal orientation with respect to the edge, including:
   resilient fastener means for engaging the portable device;
   a planar member extending from the fastener means and spaced from the portable device when the clip is fastened to the portable device;
   a slot extending through the planar member and across a substantial portion of the planar member at approximately a 45° angle to peripheral edges of the planar member, to form a pair of clip members; said slot extends through one peripheral edge of the planar member;
   a tab extending from each clip members for engaging the portable wearable device; and
   a large aperture extending through the planar member and communicating with an end of the slot.

9. The one-piece bi-directional clip of claim 8 wherein the planar member is generally rectangular and the slot extends from a first corner of the planar member toward a second, opposite corner of the planar member.

10. The one-piece bi-directional clip of claim 9 wherein the tab on each clip member is positioned adjacent the slot, at the first corner.

11. The one-piece bi-directional clip of claim of claim 9 wherein the fastener means includes a resilient and generally U-shaped member having inwardly facing lugs for engaging opposite sides of the portable device.

12. The one-piece bi-directional clip of claim 11 wherein the planar member further includes third and fourth corners and wherein the inwardly facing lugs are positioned generally at the second, third and fourth corners of the planar member.

* * * * *